United States Patent [19]
Lewis et al.

[11] Patent Number: 5,941,468
[45] Date of Patent: Aug. 24, 1999

[54] WASTE TREATMENT APPARATUS AND METHOD

[75] Inventors: Robert W. Lewis, Morgantown; Randall G. McKee, Chester Springs, both of Pa.

[73] Assignee: Sterile Technology Industries, Inc., West Chester, Pa.

[21] Appl. No.: 09/010,917

[22] Filed: Jan. 22, 1998

[51] Int. Cl.⁶ .................................................. B02C 19/12
[52] U.S. Cl. .................. 241/17; 241/18; 241/23; 241/24.11; 241/27; 241/41; 241/65; 241/186.5; 241/606
[58] Field of Search ................................ 241/17, 23, 18, 241/24.11, 41, 65, 186.5, 606, 27, 21

[56] References Cited

U.S. PATENT DOCUMENTS

| | | |
|---|---|---|
| 2,708,074 | 5/1955 | Hoskins . |
| 2,731,208 | 11/1956 | Dodd . |
| 4,578,185 | 3/1986 | Wilson et al. . |
| 4,670,227 | 6/1987 | Smith . |
| 4,884,756 | 12/1989 | Pearson . |
| 5,048,766 | 9/1991 | Gaylor et al. . |
| 5,087,420 | 2/1992 | Jackson . |
| 5,089,228 | 2/1992 | Meijer . |
| 5,116,574 | 5/1992 | Pearson . |
| 5,167,372 | 12/1992 | Poggie et al. ............................ 241/23 |
| 5,277,136 | 1/1994 | Davis . |
| 5,346,142 | 9/1994 | Miller et al. . |
| 5,360,594 | 11/1994 | Meijer . |
| 5,362,443 | 11/1994 | Tanaka et al. . |
| 5,364,589 | 11/1994 | Buehler et al. . |
| 5,384,092 | 1/1995 | Sawhill et al. . |
| 5,389,347 | 2/1995 | Hall . |
| 5,427,737 | 6/1995 | Glazer et al. ......................... 241/606 X |
| 5,470,022 | 11/1995 | Wright et al. . |
| 5,566,890 | 10/1996 | Ricciardelli . |
| 5,570,845 | 11/1996 | Lewis et al. . |
| 5,635,122 | 6/1997 | Vezzani ................................. 264/115 |
| 5,649,785 | 7/1997 | Djerf et al. .................. 241/DIG. 38 X |

FOREIGN PATENT DOCUMENTS

WO 93/06931  4/1993  WIPO .

OTHER PUBLICATIONS

Description Sheet Vincent Horizontal Press, date unknown.
"Steam Sterilization for Infectious Waste Management", GTH Roland North America, Inc. date unknown.
Infectious Waste Processor Model IWP–1000, Mediclean Technology, Inc. date unknown.
"San–I–Pak", San–I–Pak Incorporated, Date unknown.
ABB Sanitec "MICROLOOK", Date unknown.
"Summary Update of Alternative Regulated Medical Waste Treatment Systems", Lawrence G. Doucet, P.E., pp. 1–8, Nov. 1993.

*Primary Examiner*—John M. Husar
*Attorney, Agent, or Firm*—Howson and Howson

[57] ABSTRACT

Containerized medical waste is treated by shredding, and then passing the shredded material, by means of a screw conveyor, through a direct steam impingement stage and a dehydration stage in which the material is brought into contact with a hot surface to vaporize moisture and thereafter passed through a low pressure chamber in which the vapor is drawn off.

12 Claims, 1 Drawing Sheet

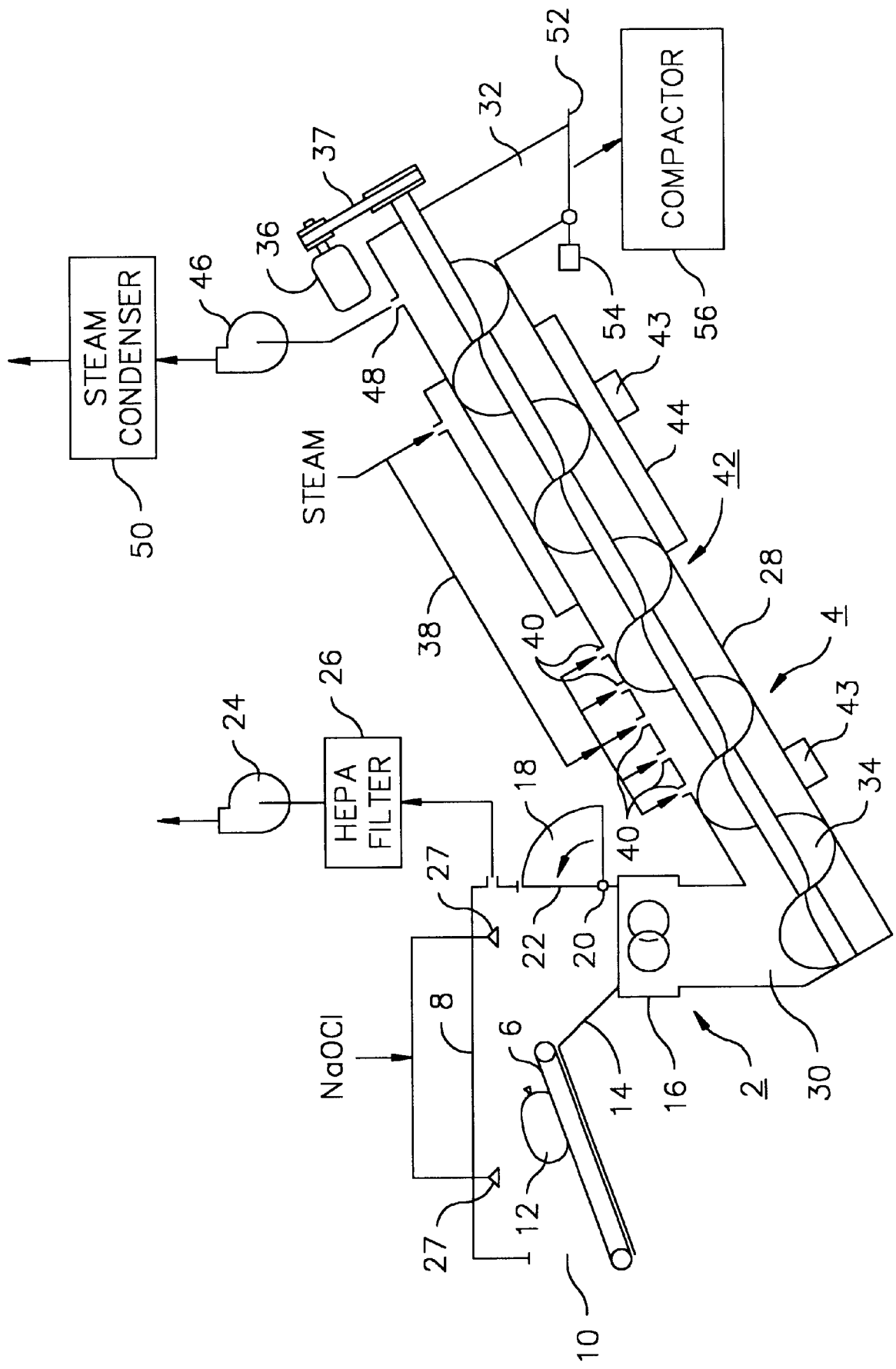

WASTE TREATMENT APPARATUS AND METHOD

SUMMARY OF THE INVENTION

This invention relates generally to waste treatment, and more particularly to a method and apparatus for the treatment of regulated medical waste such as hospital waste.

A waste treatment apparatus of the kind to which this invention relates is typically located at a commercial medical waste disposal plant, or on site at a hospital or other medical facility. All potentially infectious waste material produced in the operations of the facility is treated in the waste treatment apparatus. The apparatus delivers a product which can be compacted, held safely in conventional trash containers, and transported in conventional trash trucks or roll-off containers for disposal in landfills or similar facilities.

In the treatment of infectious waste for disposal, it is important to ensure that the ultimate waste product which is to be discarded is free of pathogenic microorganisms. It is also highly desirable, and in some instances required by law, to render the waste material in a condition such that individual components, such as disposable syringes, bandages, and body fluid receptacles are unrecognizable.

In the past, medical waste was usually incinerated. However, environmental regulations have severely limited the use of incineration for medical waste disposal. Alternative treatment methods, including steam autoclaving and chemical treatment have been used. Some of these methods are less than entirely effective in destroying pathogenic organisms. Other effective methods, require equipment which tends to be expensive to install and both expensive and difficult to operate. Another problem encountered in the operation of medical waste treatment systems is that sometimes odors and noxious gases, liquids and solid particles are exhausted to the atmosphere or discharged to sanitary sewage systems.

Many of the problems encountered in the past in the treatment of medical waste have been addressed in U.S. Pat. No. 5,570,845, granted to Sterile Technology Industries, Inc. on Nov. 5, 1996. The patent describes a process and apparatus in which containerized medical waste is carried by a conveyor under a negative pressure to a multiple-stage shredder. A sanitizing solution is added at several points in the shredder section of the apparatus. The output of the shredder is compressed and the liquid component which is separated out is recirculated. The compressed solid is conveyed through a conveyor in which the temperature of the waste is maintained at a level just under 212° F. by the introduction of steam. The pressure is maintained at or below atmospheric pressure at all points in the system to prevent release of contaminated materials into the atmosphere. By using the combination of a sanitizing solution and steam, it is possible to eliminate live microorganisms entirely while still taking advantage of negative pressure to avoid accidental release of contaminated materials. The entire disclosure of U.S. Pat. No. 5,570,845 is incorporated into this specification by reference.

This invention is an improvement over the apparatus and method described in U.S. Pat. No. 5,570,845. A drawback of the patented apparatus is that the waste material which it delivers, although entirely free of live pathogenic microorganisms, contains substantial quantities of moisture, a large portion of which comes from the steam used to effect treatment. Thus, whereas the application of steam directly to the waste material has certain advantages, it also has the disadvantage that it adds weight to the processed waste material, which results in increased residual waste transportation costs.

The principal object of this invention, therefore, is to provide an improved treatment system for infectious waste, which assures complete destruction of pathogenic microorganisms and renders the waste materials unrecognizable, and which is an improvement over prior systems in that it produces a waste product having a low moisture content.

A preferred waste treatment apparatus in accordance with the invention comprises an elongated enclosure having an entrance at one end for receiving shredded waste material, and an exit at its opposite end for delivering treated waste material. A conveyor, preferably a rotating screw conveyor, moves shredded waste material through the enclosure from the entrance to the exit. A conduit is connected from a steam supply to the interior of the enclosure for bringing steam into direct contact with the waste material in a first section of the enclosure extending from a location adjacent to the entrance to an intermediate location between the entrance and the exit. Waste material within the a second section of the enclosure along a portion of the length thereof between the intermediate location and the exit, is dehydrated by heating, preferably by a steam jacket surrounding the enclosure. Generally, the same steam source is used to supply steam to the steam jacket and to supply steam for direct contact with the waste material.

In a preferred embodiment, a blower is connected to the interior of the enclosure at a location spaced from the first section thereof. The blower establishes a pressure lower than atmospheric pressure within a part of the enclosure for removing moisture and water vapor from the waste material. The blower is preferably connected to interior of the enclosure at a location between the steam jacket and the exit, so that the part of the enclosure having a lower-than-atmospheric pressure is a distinct third section serving as a low pressure chamber.

The apparatus makes it possible to carry out a novel process for treating infectious waste material comprising the steps of: shredding the waste material; contacting the shredded waste material directly with steam at a temperature such that the waste material is maintained at an elevated temperature of at least approximately 205° F. but less than 212° F. for an interval of at least thirty minutes; and thereafter dehydrating the waste material by contacting the waste material with a surface heated to a temperature greater than 212° F., preferably to a temperature in the range of 220° F. to 235° F. In the dehydrating step, the waste material is preferably exposed to a pressure below atmospheric pressure for removal of moisture. When the shredded waste material is continuously transported, by a rotating screw conveyor, through the steam contact stage and through the dehydrating stage the shredded waste material is mixed by the screw conveyor to enhance permeation of the waste material by the steam in the steam contact stage, and to enhance contact of the waste material with the heated surface in the dehydrating stage.

The shredding step is preferably carried out in a shredding apparatus into which a sanitizing solution is sprayed periodically to prevent the formation of colonies of microorganisms.

The waste treatment apparatus and process of this invention incorporate mechanical shredding, direct steam impingement and dehydration to produce effective and efficient destruction of pathogenic microorganisms, and delivering a waste product that is comparatively light in weight by virtue of its lower moisture content, and therefore more easily transported.

Other objects, details and advantages of the invention will be apparent from the following detailed description when read in conjunction with the drawings.

BRIEF DESCRIPTION OF THE DRAWINGS

The single FIGURE is a schematic diagram of a preferred waste treatment apparatus in accordance with the invention.

DETAILED DESCRIPTION

The complete treatment apparatus embodying the invention comprises two principal components: a shredding apparatus 2 and a heat treatment apparatus 4, through which shredded waste is conveyed slowly while being subjected to direct steam impingement and dehydration.

In the embodiment if treatment apparatus illustrated in the drawing, the shredding apparatus 2 includes an inclined belt conveyor 6 inside a housing 8. The conveyor receives waste material, typically bags, boxes or "sharps" containers of regulated medical waste, through an intake opening 10. A bag of waste 12 is shown on the conveyor. Alternatively, other forms of conveyor can be used to carry the waste material into the apparatus. For example, a cart elevator, a dumper, a combination cart elevator and dumper, or other suitable conveyor can be used instead of the belt conveyor.

A hopper section 14 underneath the upper end of the conveyor conducts the packaged waste to a shredding mechanism 16 comprising conventional, cooperating rotating cutters. The shredding mechanism can be made in a variety of configurations which can be selected depending on the materials being handled. For example it can include a two-shaft or four-shaft shredder, or plural two-shaft shredders or any of many other shredder configurations.

A reciprocating ram mechanism 18, on a hinge 20, includes a pusher plate 22, which assists gravity in moving waste into the shredding mechanism by applying downward pressure to the waste containers in the hopper section 14. Other forms of rams, for example, piston rams, can be used A blower 24 draws air from the housing 8 through a high efficiency particulate air (HEPA) filter 26. This maintains an inward flow of air through the intake opening 10, thereby preventing particles from being discharged through the intake opening. An interlock (not shown) is preferably provided for preventing the introduction of raw waste material unless the blower 24 is drawing air through the intake opening.

Sanitizing spray nozzles 27 introduce a sanitizing solution (preferably sodium hypochlorite in water) into the housing 8 intermittently, to prevent the growth of colonies of microorganisms in the housing 8 and in the shredding apparatus 16.

The heat treatment apparatus 4 comprises an inclined, elongated enclosure 28 having an entrance opening 30 at its lower end for receiving shredded waste material from the shredding mechanism 16, and an exit opening 32 at its upper end for discharging processed waste material.

The elongated enclosure preferably has a cylindrical inner wall, and a helical screw conveyor 34 extending through it for moving the shredded waste material from the entrance opening 30 to the exit opening 32. The helical screw conveyor preferably fits into the enclosure with a small clearance between its blade and the cylindrical inner wall of the enclosure. It is rotated by a motor 36 through a chain 37.

Steam, supplied through a conduit 38, is injected, at a pressure below 15 psi, into the interior of enclosure 28 through a plurality of injection ports 40 spaced from one another in the longitudinal direction at locations between the entrance opening 30 and an intermediate location 42 between the entrance and the exit opening. The steam injection ports bring steam into direct contact with the shredded waste material within a direct steam impingement section of the enclosure extending from a location adjacent to entrance opening 30 to the intermediate location 42.

The screw conveyor 34 agitates and tumbles the shredded waste material to enhance contact between the steam and the waste material. Mixing tabs (not shown) can be provided on the screw conveyor to enhance permeation of the waste by the steam. The speed of the screw conveyor is controlled so that the residence time of the waste material in the steam impingement section is approximately thirty minutes. Thermocouples 43 are provided on the bottom of the enclosure 28. A first such thermocouple operates a valve (not shown) which controls the flow of steam to maintain the temperature of the waste material along the length of the steam impingement stage in the range of 205° F. to 212° F., and preferably between 205° F. and 210° F.

Beyond the intermediate location 42, a steam jacket 44 surrounds the enclosure 28. The steam jacket preferably receives steam at low pressure from the same source that supplies steam to the direct impingement stage. The steam in the steam jacket is maintained at a temperature such that the surface of the inner wall of the enclosure 28 is held at a temperature above 212° F., and preferably at a temperature in the range of 220° F. to 235° F. The steam is preferably delivered at a temperature of 235° F., and condenses on the waste at a temperature in the range of 205° F. to 212° F. The steam temperature in the jacket is controlled by a second thermocouple 43, which is located on or within the steam jacket and operates a valve (not shown) to control the flow of steam.

The action of the screw conveyor ensures good contact between the waste and the hot cylindrical inner wall of enclosure 28. Thus, the steam jacket provides a second stage of treatment in which the waste is brought into contact with a hot surface so that moisture in the waste material is converted to vapor. This stage serves to dehydrate the waste material, reducing its weight.

To prevent the moisture in the vapor generated by the heat of the steam jacket from returning to the waste, moisture is exhausted from the interior of the enclosure, at a location between the steam jacket and the exit, by a blower 46, which is connected to a port 48. The steam is either vented to the atmosphere, or a condenser 50 at the outlet of the blower 46 may be used to return water to the steam supply. The condenser is particularly useful if the apparatus is located within a building. The exhaustion of moisture takes place by virtue of the low pressure maintained by blower 46 in the enclosure near its exit opening 32. A flapper 52, with a counterweight 54, normally maintains the exit opening in a closed condition so that low pressure chamber can be maintained at the upper end of the conveyor. However, as waste material accumulates within the exit opening, the flapper opens under the weight of the waste material, permitting the waste material to be discharged to a compactor 56.

The dehydration of the waste material is initiated by the heat imparted to it by the steam jacket, and completed by the exhaustion of water vapor from the low pressure chamber. Thus, in the preferred embodiment of the invention, the section surrounded by the steam jacket and the low pressure chamber, together constitute a dehydration stage.

The waste treatment apparatus does not depend on chemical application for sterilization. The sanitizing spray merely prevents the build-up of colonies of microorganisms in the feed and shredding mechanisms, and introduces minimal amounts of moisture into the waste. The minimization of moisture introduction in the preliminary stages improves the transfer of heat in the direct steam impingement. It also improves the efficiency of the dehydration stage in destroying pathogenic microorganisms, and delivering a lightweight waste product. The direct impingement of steam onto the waste material helps to ensure complete destruction of live microorganisms. Moisture introduced into the waste material in the direct steam impingement stage is removed in the dehydration stage of the apparatus.

Various modifications can be made to the apparatus described. For example the screw conveyor can comprise two or more sections separately controlled. Various other modifications can be made to the apparatus, and to the process for which it is used, without departing from the scope of the invention as defined in the following claims.

We claim:

1. Waste treatment apparatus comprising:
    an elongated enclosure having an entrance at one end for receiving shredded waste material, an interior wall and an exit at its opposite end for delivering treated waste material;
    a conveyor for moving shredded waste material through the elongated enclosure from the entrance to the exit;
    a steam supply;
    a conduit connected from the steam supply to the interior of the enclosure for bringing steam into direct contact with the waste material in a first section of the enclosure extending from a location adjacent to the entrance to an intermediate location between the entrance and the exit;
    a steam jacket surrounding a second section of the enclosure along a portion of the length thereof between the intermediate location and the exit, for heating the interior wall of the enclosure at the location of said second section and thereby heating waste material within said second section;
    means for introducing steam into the steam jacket at a temperature such that the temperature of the interior wall at the location of said second section is maintained between 212° F. and 235° F. throughout the passage of waste material through said second section; and
    a blower, connected to the interior of the enclosure at a location spaced from the first section of the enclosure, for establishing within a part of the enclosure a pressure lower than atmospheric pressure for removing moisture from the waste material.

2. A waste treatment apparatus according to claim 1, in which the second section of the enclosure surrounded by the steam jacket is spaced from the exit, and said blower is connected to the interior of the enclosure at a location between the steam jacket and the exit.

3. A waste treatment apparatus according to claim 1, in which the conveyor comprises a screw conveyor extending lengthwise through the elongated enclosure.

4. A waste treatment apparatus according to claim 1, in which the conveyor is a screw conveyor extending lengthwise at least through the first and second sections of the enclosure.

5. A waste treatment apparatus according to claim 1, in which the steam jacket is connected to the steam supply to receive steam therefrom.

6. A waste treatment apparatus according to claim 1, including a shredder arranged to deliver shredded waste material to the entrance of the elongated enclosure, a feed conveyor for delivering waste material to the shredder, a housing surrounding at least a part of the feed conveyor and enclosing a path extending from the feed conveyor to the shredder, and a blower connected to the housing for maintaining a flow of air to the housing.

7. Waste treatment apparatus comprising:
    an elongated enclosure having an entrance at one end for receiving shredded waste material, and an exit at its opposite end for delivering treated waste material;
    a conveyor for moving shredded waste material through the elongated enclosure from the entrance to the exit;
    a steam supply;
    a conduit connected from the steam supply to the interior of the enclosure for bringing steam into direct contact with the waste material in a first section of the enclosure extending from a location adjacent to the entrance to an intermediate location between the entrance and the exit;
    a steam jacket surrounding a second section of the enclosure along a portion of the length thereof between the intermediate location and the exit, for heating waste material within said second section;
    a blower, connected to the interior of the enclosure at a location spaced from the first section thereof, for establishing within a part of the enclosure a low pressure chamber, in which the pressure is lower than atmospheric pressure for removing moisture from the waste material; and
    a compactor connected to receive dehydrated waste material from the low pressure chamber.

8. Waste treatment apparatus comprising:
    means providing an enclosed path for the travel of shredded waste material, having an entrance at one end for receiving shredded waste material, and an exit at its opposite end for delivering treated waste material;
    means for moving shredded waste material through the enclosed path from the entrance to the exit;
    means for bringing steam into direct contact with the waste material in a first section of the enclosed path extending from a location adjacent to the entrance to an intermediate location between the entrance and the exit;
    means for heating waste material within a second section of the enclosed path downstream from the first section in the direction of travel of the shredded waste material, said means for heating waste material within said second section comprising a surface arranged to be contacted by said waste material as it travels through said second section; and means for heating said surface to a temperature in the range from 212° F. to 235° F. and maintaining said surface at a temperature within said range throughout the passage of waste material through said second section; and
    means connected to the interior of the enclosure at a location spaced from the first section of the enclosure, for establishing within a part of the enclosure a pressure lower than atmospheric pressure for removing moisture from the waste material.

9. A process for treating infectious waste material comprising the steps of:
    shredding the waste material;
    contacting the shredded waste material directly with steam at a temperature such that the waste material is maintained at an elevated temperature of at least approximately 205° F. but less than 212° F. for an interval of at least thirty minutes; and thereafter dehydrating the waste material by contacting the waste material with a surface heated to a temperature greater than 212° F. and exposing the waste material to a pressure lower than atmospheric pressure by means of a blower, whereby the lower-than-atmospheric pressure assists the heated surface in removing moisture from the waste material and the moisture released from the waste material by contact with said heated surface is carried away from the waste material by the blower.

10. The process of claim 9, in which the shredded waste material is continuously transported, by a rotating screw conveyor, through a steam contact stage wherein the contacting step takes place, and through a dehydrating stage wherein the dehydrating step takes place, and in which the shredded waste material is also mixed by the screw conveyor to enhance permeation of the waste material by the steam in the steam contact stage, and to enhance contact of the waste material with the heated surface in the dehydrating stage.

11. The process of claim 9, in which the surface with which the waste material is contacted in the dehydrating step is maintained at a temperature in the range of approximately 220° F. to 235° F.

12. The process of claim 9, in which the shredding step is carried out in a shredding apparatus, and in which a sanitizing solution is sprayed periodically into the shredding apparatus to prevent the formation of colonies of microorganisms in the shredding apparatus.

* * * * *